United States
Briedis et al.

4,033,976

July 5, 1977

[54] COPPER-OXAZOLINE COMPLEX

[75] Inventors: Juozas Briedis, Lemont; Louis A. Jurisch, Marengo, both of Ill.

[73] Assignee: IMC Chemical Group, Inc., Terre Haute, Ind.

[22] Filed: Oct. 28, 1975

[21] Appl. No.: 626,607

[52] U.S. Cl. .............................. 260/299; 106/15 R
[51] Int. Cl.² .......................................... C07F 1/08
[58] Field of Search .................. 260/299; 424/294

[56] References Cited

UNITED STATES PATENTS

| | | | |
|---|---|---|---|
| 2,533,744 | 12/1950 | Skinner et al. | 424/294 |
| 3,178,421 | 4/1965 | Konishi et al. | 260/299 |
| 3,248,397 | 4/1966 | Purcell | 260/307 |

*Primary Examiner*—Donald G. Daus
*Assistant Examiner*—D. B. Springer
*Attorney, Agent, or Firm*—Robert H. Dewey; Howard E. Post

[57] ABSTRACT

A complex of copper and an oxazoline having utility in anti-fouling paints for the marine industry.

14 Claims, No Drawings

COPPER-OXAZOLINE COMPLEX

BACKGROUND OF THE INVENTION

This invention relates to an organo-copper complex. In a particular aspect this invention relates to an oil-dispersible complex of copper and an oxazoline.

The fouling of boat hulls and other objects immersed in sea water is a severe problem. The fouling is caused by the growth of marine organisms, such as barnacles, encrusting bryozoans, hydroids, algae, etc. These organisms are highly susceptible to copper and mercury and accordingly it is conventional practice to incorporate oxides of these metals in protective coatings to be applied to the immersed objects.

SUMMARY OF THE INVENTION

It is an object of this invention to provide a novel organo-copper complex.

It is another object of this invention to provide an organo-copper complex useful in anti-fouling paints.

Other objects of this invention will be apparent to those skilled in the art from the disclosure herein.

It is the discovery of this invention that copper forms a complex with a mono-oxazoline represented by formula I or a bis-oxazoline represented by formula II:

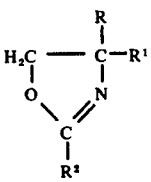

(I)

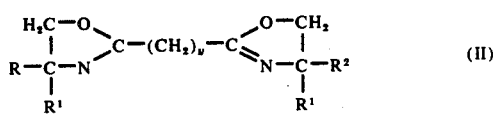

(II)

where R and $R^1$ can be alkyl of 1–3 carbon atoms or hydroxymethyl and can be the same or different; $R^2$ is alkyl of from 1 to 4 carbon atoms or alkenyl of 2–4 carbon atoms; y is an integer of 1 to 4. The compounds prepared from an oxazoline of formula I can be represented by the formula:

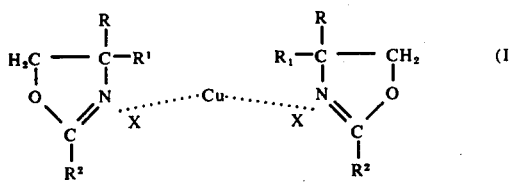

(III)

where X is the anion of the copper salt used to form the chelate. The compounds prepared from an oxazoline of formula II can be represented by the formula:

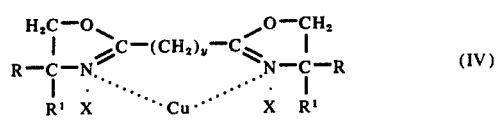

(IV)

R, $R^1$, $R^2$, X and y have the same meanings hereinbefore set forth. These compounds have utility as antifouling agents in marine finishes for boats and the like.

DETAILED DISCUSSION

The complexes of the present invention are readily formed by contacting at least one molar equivalent of a suitable cupric salt with 2-molar equivalents of an oxazoline represented by the foregoing formula I, or with one molar equivalent of an oxazoline represented by formula II. Preferably the compounds are contacted in the presence of a suitable solvent, e.g. water or lower alkanol of 1 to 3 carbon atoms. When $R^2$ is alkyl or alkenyl of 1 to 3 carbon atoms, the oxazoline is sufficiently soluble that water is a suitable solvent, but when $R^2$ is of 4 carbon atoms, a lower aliphatic alcohol is preferred, e.g. methanol, ethanol, or 1 or 2-propanol. Many suitable salts of copper are known, including but not limited to cupric acetate, chloride, bromide, nitrate, formate and sulfate. Accordingly X in formulas II, III and IV can be acetate, chlorine, bromine, nitrate, formate or sulfate. The acetate, chloride, bromide, nitrate and formate salts of copper are soluble in lower aliphatic alcohols to a limited extent and these alcohols can be used as solvents when water is unsuitable. Methanol is a preferred alcohol. The oxazolines are very soluble in alcohols.

The precipitated copper complex, which is believed to be a chelate, can be separated by any convenient method, e.g. by filtration, decantation or centrifugation. It is preferably dried, e.g. by heating for a suitable period, and comminuted before being used in an antifouling paint.

The copper complex of the present invention can be employed with any of the anti-fouling paints, many of which are known in the art. Generally, but not necessarily, the copper complex will be used to replace from 10–25% or up to 50% of the cuprous oxide and/or mercuric oxide previously used on an equal weight basis.

The oxazolines of the present invention are known in the art and can be prepared by the method of Purcell, U.S. Pat. No. 3,248,397 which is incorporated herein by reference thereto.

The invention will be better understood with reference to the following examples. It is understood however that these examples are intended for illustration only and it is not intended that the invention be limited thereby.

EXAMPLE 1

Cupric chloride ($CuCl_2 \cdot H_2O$) 17 g (0.1 mole) was dissolved in 183 g of distilled water and 2,4-diethyl-4-hydroxymethyl-2-oxazoline 15 g (0.09 mole) was added with stirring. There was obtained copper-oxazoline precipitate represented by formula III. It was isolated by centrifugation.

An anti-fouling paint was prepared according to Federal Specification TT-P-1174, as follows:

| MATERIALS | PARTS BY WEIGHT |
| --- | --- |
| Zinc Oxide | 200.0 |
| Iron Oxide | 90.0 |
| Talc | 80.0 |
| Cuprous Oxide | 400.0 |
| Mercuric Oxide | 20.0 |
| Rosin | 270.0 |
| Pine Oil | 40.0 |
| Coal Tar | 64.0 |
| Mineral Spirits | 286.0 |
| | 1,450.0 |

This paint was used as the control in this test and throughout the rest of the examples.

Another batch of the paint was similarly prepared except that 10% of the cuprous oxide was replaced with a like amount of the copper-oxazoline complex using a steel ball mill to disperse the complex in the coating.

Each of these coatings was used for coating a fiberglass panel. The panel was thoroughly sanded, then coated by brushing with each of the coatings. The coated panels were dried for one day, then a second coat was applied. The panels were then dried for a week, following which they were immersed in the sea water of the east Florida coast.

The panels were inspected monthly, except for the third month, and evaluated as to surface fouling by marine organisms, fouling resistance and the condition of the anti-fouling coating. On the basis of these factors, the coatings were finally rated for over-all performance. The results, which are summarized in Table 1, show that the coating wherein the copper-oxazoline complex was substituted for 10% of the cuprous oxide had satisfactory anti-fouling properties and the copper oxazoline complex has utility as an anti-fouling agent.

TABLE 1

| | EVALUATION OF ANTI-FOULING COATINGS | | | | |
|---|---|---|---|---|---|
| | Months Exposure to Sea Water | | | | |
| Example | 1 | 2 | 4 | 5 | 6 |
| Control | 90 | 90 | 90 | 90 | 80 |
| 1 | 95 | 95 | 90 | 90 | 90 |
| 2 | 95 | 95 | 95 | 79 | 70 |
| 3 | 85 | 88 | 75 | 55 | 0 |
| 4 | 95 | 95 | 95 | 95 | 80 |
| 5 | 95 | 95 | 75 | 52 | 0 |

EXAMPLES 2-3

The experiment of Example 1 was repeated in all essential details except that 25 and 50%, respectively, of the cuprous oxide was replaced by the copper-oxazoline complex. The results are summarized in Table 1. It is apparent from the results in Table 1 that the copper oxazoline complex can replace up to 25% of the cuprous oxide. However, some cuprous oxide is required because at 50% replacement, there is a diminution of anti-fouling activity.

EXAMPLES 4-5

A bis-oxazoline represented by formula II was prepared by a known method by reacting 2-amino-2-methyl-1-propanol with glutaric acid in a 2:1 mole ratio. In the resulting compound, R and $R^1$ are methyl and y is 3.

The experiment of Example 1 was repeated in all essential details except that cupric chloride and the bis-oxazoline prepared above were reacted in a 1:1 mole ratio to give a compound represented by the formula IV where R, $R^1$ and y have the same meanings defined above and X is chlorine. This compound, 40 g, was used to replace 40 g (10%) of cuprous oxide in Example 4 and in Example 5, 100 g was used to replace 100 g (25%) of the cuprous oxide.

The results are given in Table 1. The coating of Example 4 out-performed the control but the coating of Example 5 began to lose effectiveness between the 2nd and 4th month.

EXAMPLES 6-10

The experiment of Example 1 is repeated in all essential details except that up to 25% of the cuprous oxide is replaced with a copper-oxazoline complex represented by formula III wherein R, $R^1$, $R^2$ and X have the meanings set forth in Table 2.

TABLE 2

| Example | R | $R^1$ | $R^2$ | X |
|---|---|---|---|---|
| 6 | $CH_3$ | $CH_3$ | $CH_3$ | $CH_3COO$ |
| 7 | $CH_2OH$ | $CH_3$ | $C_3H_7$ | $NO_3$ |
| 8 | $CH_2OH$ | $CH_2OH$ | $C_4H_9$ | $HCOO^-$ |
| 9 | $CH_2OH$ | $C_2H_5$ | $C_3H_6$ | $SO_4$ |
| 10 | $CH_2OH$ | $CH_2OH$ | $C_2H_4$ | Cl |

The copper-oxazoline salts are useful as anti-fouling agents in an amount up to 25% of the cuprous oxide usually used.

EXAMPLES 11-13

The experiment of Example 1 is repeated in all essential details except that up to 25% of the cuprous oxide is replaced with a copper-oxazoline complex represented by formula IV wherein R, $R^1$, $R^2$, y and X have the meanings set forth in Table 3.

TABLE 3

| Example | R | $R^1$ | X | y |
|---|---|---|---|---|
| 11 | $CH_2OH$ | $CH_2OH$ | $SO_4$ | 1 |
| 12 | $CH_3$ | $CH_3$ | $CH_3COO^-$ | 2 |
| 13 | $CH_2OH$ | $CH_3$ | $NO_3$ | 4 |

The copper-oxazoline complexes are useful as anti-fouling agents for replacing up to 25% of the cuprous oxide usually used.

We claim:

1. A complex of copper and an oxazoline represented by the formula

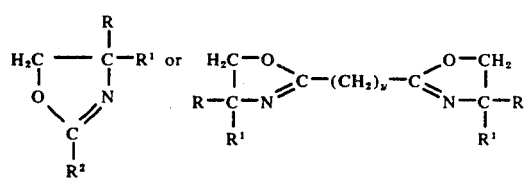

where R and $R^1$ are alkyl radicals of 1–3 carbon atoms, or hydroxymethyl and can be the same or different; $R^2$ is alkyl of from 1 to 4 carbon atoms or alkenyl of 2–4 carbon atoms; and y is an integer of 1 to 4, said complex being represented by the formula

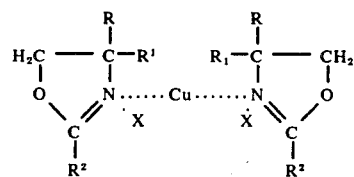

or

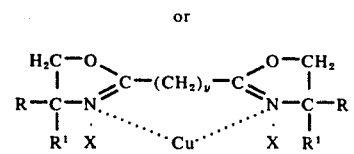

where X is an acetate, chloride, bromide, nitrate, formate or sulfate ion.

2. The complex of claim 1 wherein the oxazoline is represented by the formula

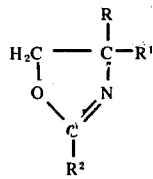

and the complex is represented by the formula

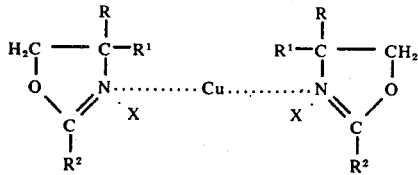

wherein R and R¹ are alkyl radicals of 1–3 carbon atoms or hydroxymethyl and can be the same or different; R² is an alkyl radical of 1–3 carbon atoms or alkenyl of 2–4 carbon atoms and X is an acetate, chloride, bromide, nitrate, formate or sulfate ion.

3. The copper-oxazoline complex of claim 2 wherein R, R¹ and R² are methyl.

4. The complex of claim 2 wherein R is methyl and R¹ and R² are ethyl.

5. The complex of claim 2 wherein R and R¹ are hydroxymethyl and R² is propenyl.

6. The complex of claim 2 wherein X is chloride ion.

7. The complex of claim 1 wherein the oxazoline is represented by the formula

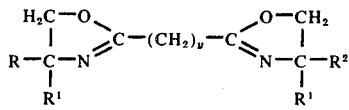

and the complex is represented by the formula

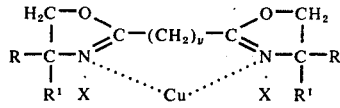

wherein R and R¹ are alkyl radicals of 1–3 carbon atoms or hydroxymethyl and can be the same or different; R² is an alkyl radical of 1–3 carbon atoms or alkenyl of 2–4 carbon atoms and X is an acetate, chloride, bromide, nitrate, formate or sulfate ion and $y$ is a integer of 1 to 4.

8. The copper-oxazoline complex of claim 7 wherein R, R¹ and R² are methyl.

9. The complex of claim 7 wherein R is methyl and R¹ and R² are ethyl.

10. The complex of claim 7 wherein R and R¹ are hydroxymethyl and R² is propenyl.

11. The complex of claim 7 wherein X is chloride ion.

12. The complex of claim 7 wherein $y$ is 1.

13. The complex of claim 7 wherein $y$ is 2.

14. The complex of claim 7 wherein $y$ is 4.

* * * * *

UNITED STATES PATENT AND TRADEMARK OFFICE
CERTIFICATE OF CORRECTION

PATENT NO. : 4,033,976
DATED : July 5, 1977
INVENTOR(S) : Juozas Briedis and Louis A. Jurisch It is certified that error appears in the above—identified patent and that said Letters Patent are hereby corrected as shown below:

Column 1, lines 36-39, that part of Formula II which reads:

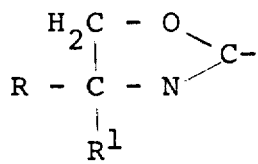     should read     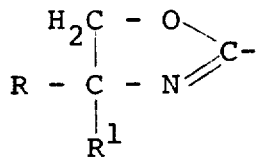

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*